US00PP35010P3

(12) United States Plant Patent
Wilson

(10) Patent No.: US PP35,010 P3
(45) Date of Patent: Feb. 28, 2023

(54) ***ALOCASIA* PLANT NAMED 'DAWN'**

(50) Latin Name: *Alocasia macrorrhiza varigata*
Varietal Denomination: 'Dawn'

(71) Applicant: Dawn F. Wilson, Miami, FL (US)

(72) Inventor: Dawn F. Wilson, Miami, FL (US)

( * ) Notice: Subject to any disclaimer, the term of this patent is extended or adjusted under 35 U.S.C. 154(b) by 0 days.

(21) Appl. No.: 17/323,485

(22) Filed: May 18, 2021

(65) Prior Publication Data

US 2022/0377956 P1 Nov. 24, 2022

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Jon M. Gibbs; Lowndes

(57) ABSTRACT

'Dawn' is a distinctive cultivar of *Alocasia* plant which is characterized by the combination of large multi-colored cordate-sagittate foliage with large and broadly-disbursed color patterns, undulate margins, helicoid-apiculate apex, reduced browning of lighter colors in sunlight, and the stability of all characteristics from generation to generation.

3 Drawing Sheets

Latin name: *Alocasia macrorrhiza variegata.*
Variety denomination: Dawn.

CROSS REFERENCE TO RELATED APPLICATIONS

Not applicable.

STATEMENT REGARDING FEDERALLY SPONSORED RESEARCH

Not applicable.

BACKGROUND OF THE INVENTION

Parentage: 'Dawn' originated as a naturally occurring, whole-plant mutation of an unnamed plant of the commercial cultivar *Alocasia macrorrhiza variegata* (not patented). In 2018, the inventor discovered the mutation at her commercial shade house in Miami, Fla., growing amongst a cultivated population of unnamed *Alocasia macrorrhiza variegata* plants. The mutation was noted for its large multi-colored cordate-sagittate foliage with large and broadly-disbursed color patterns, undulate margins, helicoid-apiculate apex, reduced browning of lighter colors in sunlight, and was subsequently isolated for further evaluation in order to confirm the distinctness and stability of the characteristics first observed. 'Dawn' was selected for commercialization after confirmation of distinctness and stability.

Asexual Reproduction: Asexual reproduction of 'Dawn', by way of division, was first initiated in the summer of 2018 at a commercial shade house in Miami, Fla. Through three years of continuous asexual reproduction, the unique features of this cultivar have proven to be stable and true to type.

BRIEF SUMMARY OF THE INVENTION

The cultivar 'Dawn' has not been observed under all possible environmental conditions. The phenotype may vary with differing environmental conditions such as temperature, duration of light exposure and level of intensity, with no variance in genotype. The following traits have been repeatedly observed and are determined to be the unique characteristics of 'Dawn'. These characteristics in combination distinguish 'Dawn' as a new and distinct *Alocasia* cultivar:

1. *Alocasia* 'Dawn' exhibits large, cordate-sagittate foliage with a helicoid-apiculate apex and undulate margins;
2. *Alocasia* 'Dawn' exhibits multi-colored foliage with larger and more broadly disbursed color patterns;
3. *Alocasia* 'Dawn' exhibits a lamina which is held upright to horizontal to pendulate, relative to the petiole; and
4. *Alocasia* 'Dawn' exhibits enhanced resistance to browning of lighter-colored areas of the foliage resulting from sun exposure.

The parent of 'Dawn' is the closest known commercial cultivar available for comparison. Compared to the parent plant, 'Dawn' has undulate leaf margins, the parent plant has slightly undulate leaf margins. The parent plant has a sagittate leaf shape whereas 'Dawn' has a cordate-sagittate leaf shape. The parent plant has a cuspidate leaf apex whereas 'Dawn' differs in that it has a helicoid-apiculate leaf apex. 'Dawn' exhibits an enhanced resistance to sun browning in the lighter colored areas of the foliage, whereas the parent plant has little to no sun browning resistance. 'Dawn' further differs from the parent plant in that it produces larger and more broadly disbursed color patterns on its foliage and not the small color patterns or single-colored leaves.

DETAILED BOTANICAL DESCRIPTION OF THE PLANT

Figure 1:
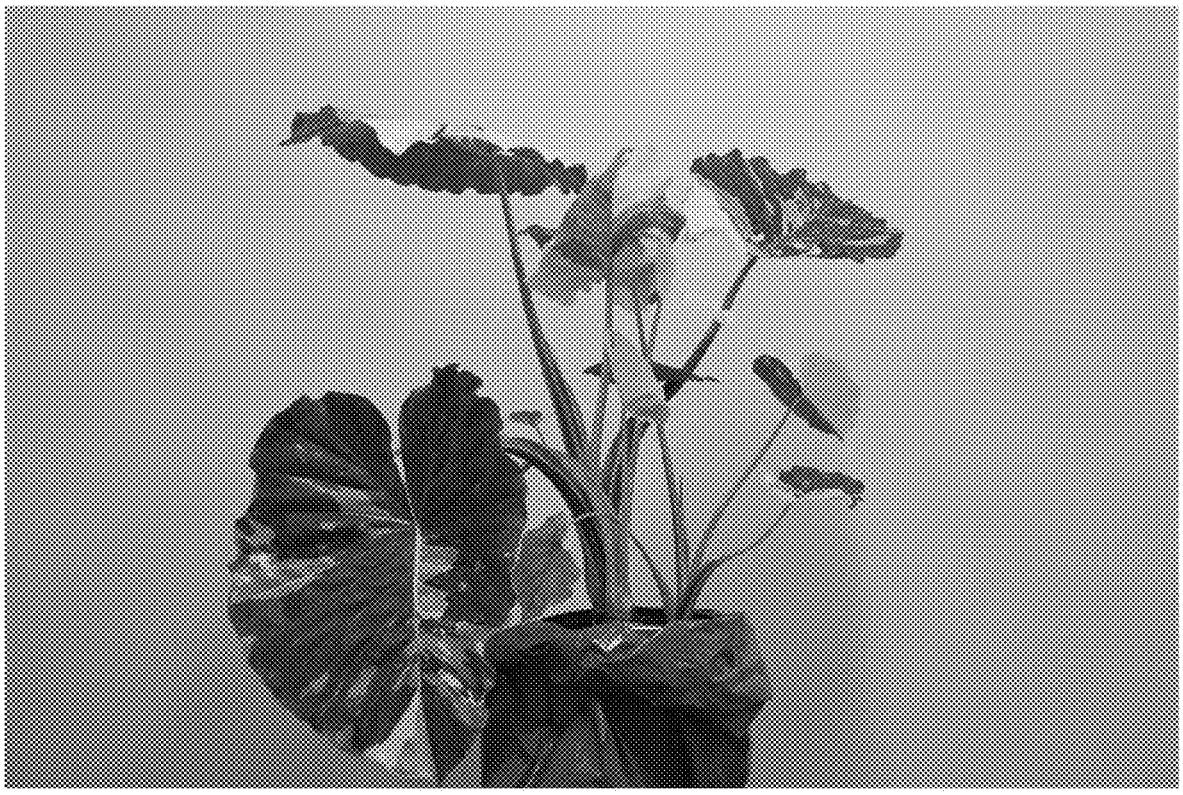
FIG. 1 illustrates, as nearly true as it is reasonably possible to make the same in color photographs of this type, four exemplary plants of 'Dawn' grown in a commercial shade house in Miami, Fla. These plants are approximately 26 weeks old, shown planted in a 25 cm container.
Figure 2:
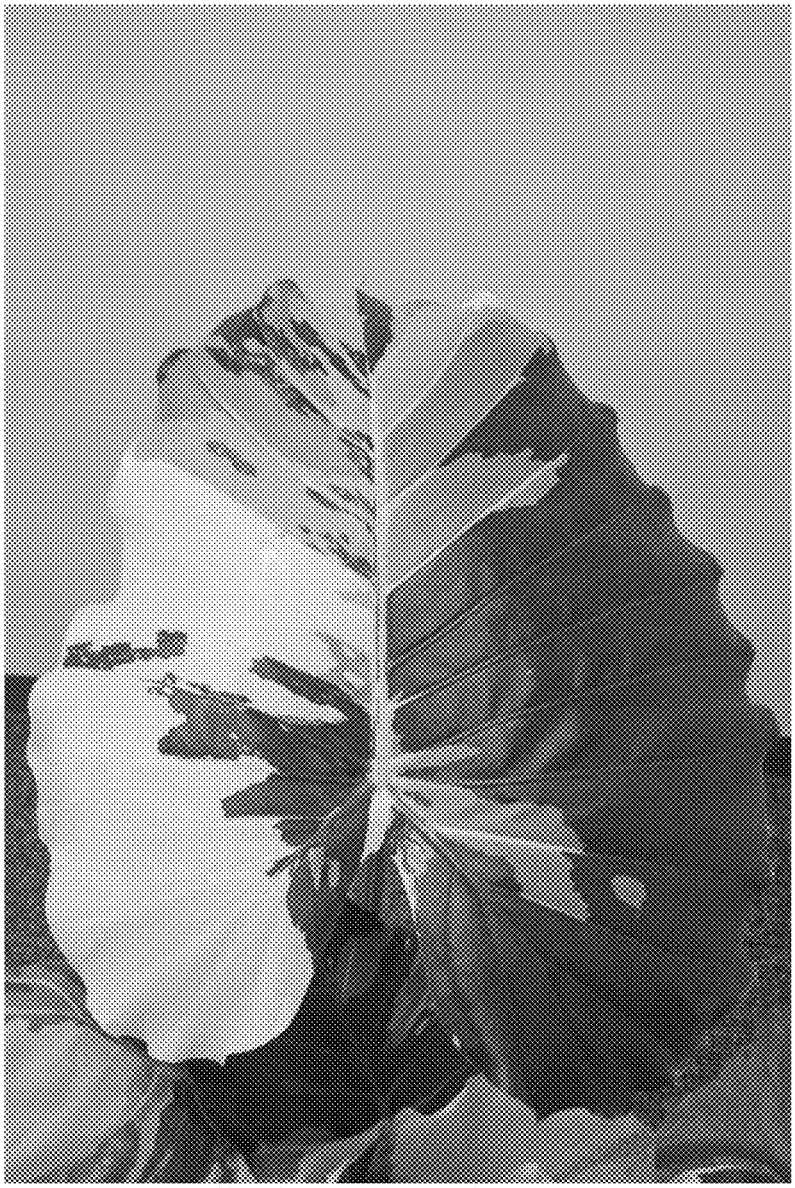
FIG. 2 illustrates, as nearly true as it is reasonably possible to make the same in color photographs of this type, the typical mature foliage of 'Dawn'.
Figure 3:
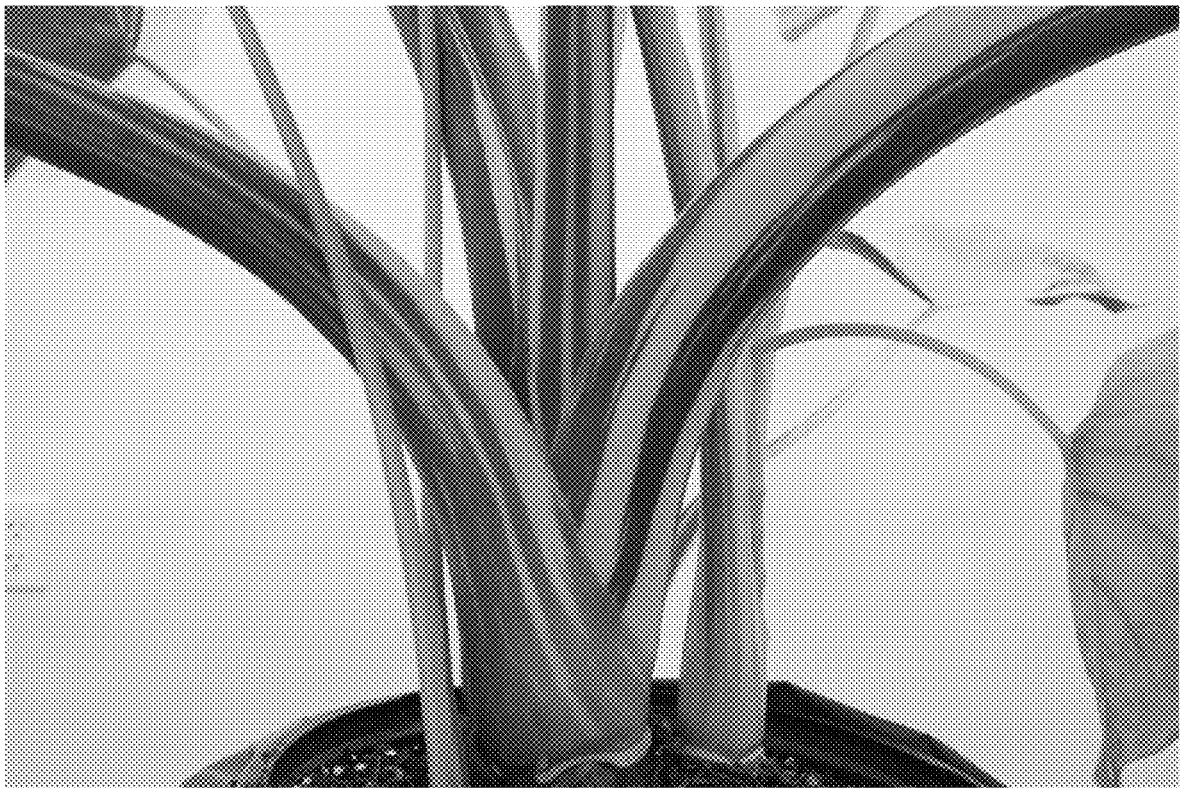
FIG. 3 illustrates, as nearly true as it is reasonably possible to make the same in color photographs of this type, the typical petiole of 'Dawn'.

The following observations and measurements made in May 2021 describe averages from two 26 week-old 'Dawn' plants grown in 25 cm nursery containers at a shadehouse in Miami, Fla. Plants were produced in a shade house with eighty percent (80%) shade covering, overhead irrigation, 18-6-8 fertilizer, and integrated pest management.

Those skilled in the art will appreciate that certain characteristics will vary with older or, conversely, with younger plants. 'Dawn' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. The color notations used herein are based on the closest comparisons to The Royal Horticultural Society Colour Chart, The Royal Horticultural Society, London, Sixth Edition (2015; 2019 reprint) ("R.H.S.").

Plant description:

*Growth habit*.—Tropical herb with an upright and generally outward growth habit.

*Plant shape*.—Broad obovate.

*Height from soil level to top of foliar plane*.—68.5 cm.

*Plant spread*.—109.5 cm.

*Growth rate*.—Moderately fast.

*Plant vigor*.—Vigorous.

*Propagation type*.—Division.

*Time to produce a finished plant*.—Approximately 26 weeks to produce a marketable finished plant in a 25 cm pot.

*Disease and pest resistance or susceptibility*.—Neither resistance nor susceptibility to pests and diseases common to *Alocasia* have been observed.

*Environmental tolerances*.—Adapt to temperatures as low as 2 degrees Celsius and as high as 35 degrees Celsius; enhanced tolerance to sunlight; moderate to high tolerance to rain; low tolerance to wind.

Roots:

*General*.—Moderately dense, moderately branched rooting; roots are fleshy.

*Distribution in the soil profile*.—Shallow to moderately deep.

*Diameter of roots*.—About 2.0 mm on average.

*Texture*.—Fleshy body with about 0.8 cm-3.1 cm long root hairs.

*Color*.—RHS 155A (Yellowish White).

Foliage:

*Quantity*.—4-5 leaves per clump.

*Arrangement*.—Alternate.

*Attachment*.—Petiolate.

*Division*.—Single.

*Lamina*.—a. Attitude: Ranging from near upright to horizontal to pendulous. b. Shape: Cordate-sagittate. c. Length: 39.6 cm, excluding the petiole. d. Width: 31.8 cm. e. Apex: Helicoid-apiculate. f. Base: Obtuse with lobes about 13.1 cm wide and 8.5 cm deep. g. Margins: Entire and slightly angular; undulate. h. Texture and luster, adaxial surface: Coriaceous, glabrous, and satiny. i. Texture and luster, abaxial surface: Coriaceous, glabrous, and satiny. j. Color: i. Juvenile foliage, adaxial surface: A blend of RHS 138A (Moderate Yellowish Green), RHS 147B (Moderate Yellow Green), RHS 147C (Moderate Yellow Green), and/or RHS 160C (Pale Greenish Yellow). ii. Juvenile foliage, abaxial surface: a blend of RHS 138A Moderate Yellowish Green), RHS 147C (Moderate Yellow Green), RHS 160C (Pale Greenish Yellow), and/or RHS 191B Greyish Yellow Green). iii. Mature foliage, adaxial surface: A blend of RHS 137A (Moderate Olive Green), RHS 138A (Moderate Yellowish Green), RHS 147B (Moderate Yellow Green) RHS 147C (Moderate Yellow Green), and/or RHS 160C (Pale Greenish Yellow). iv. Mature foliage, abaxial surface: A blend of 137B (Moderate Olive Green), 160C (Pale Greenish Yellow), and/or 191A (Greyish Yellow Green). k. Venation. i. Pattern: Pinnate. ii. Color, adaxial surfaces: A streaked blend of 139A (Dark Yellowish Green and RHS 157D (Greenish White). iii. Color, abaxial surface: A streaked blend of 139A (Dark Yellowish Green and RHS 157D (Greenish White).

*Petiole*.—a. Attitude: Upright and slightly outward to near pendulous. b. Strength: Moderately strong. c. Length: 49.5 cm from base of plant. d. Diameter: 4.1 cm at base of plant 0.9 cm at base of blade. e. Texture and luster, adaxial surface: Smooth, glabrous and satiny. f. Texture and luster, abaxial surface: Smooth, glabrous and satiny. g. Color, adaxial surface: A streaked blend of RHS 138A (Moderate Yellowish Green) and RHS 157A (Pale Yellow Green). h. Color, abaxial surface: A streaked blend of RHS 138A (Moderate Yellowish Green) and RHS 157A (Pale Yellow Green).

Inflorescence: To date, 'Dawn' has not flowered.

COMPARISONS WITH THE PARENT PLANTS

Compared against the parent plant, an unnamed *Alocasia macrorrhiza variegata* plant (not patented), plants of the new cultivar 'Dawn' differ in the characteristics described in TABLE 1 below.

TABLE 1

| Characteristic | 'Dawn' | Parent Plant |
|---|---|---|
| Leaf margin | undulate | slightly undulate |
| Leaf shape | cordate-sagittate | sagittate |
| Leaf apex | helicoid-apiculate | cuspidate |
| Sun Browning | enhanced resistance | little to no resistance |
| Leaf coloring | larger and more broadly disbursed color patterns | Small color patterns or single-color leaves |

What is claimed is:

1. A new and distinct variety of *Alocasia* plant named 'Dawn', substantially as described and illustrated herein.

* * * * *